(12) United States Patent
Fang

(10) Patent No.: US 8,431,338 B2
(45) Date of Patent: Apr. 30, 2013

(54) SELF-DIRECTING AND SELF-ASSEMBLING NANOMEDICINE INTO QUANTIZED CONDUCTANCE JUNCTIONS AND ITS PROCESS

(75) Inventor: Yan Fang, Shanghai (CN)

(73) Assignee: Zhonshan Hospital, Fudan University, Shanghai (CN)

( * ) Notice: Subject to any disclaimer, the term of this patent is extended or adjusted under 35 U.S.C. 154(b) by 1278 days.

(21) Appl. No.: 11/886,490

(22) PCT Filed: Jan. 23, 2006

(86) PCT No.: PCT/CN2006/000108
§ 371 (c)(1),
(2), (4) Date: Nov. 19, 2007

(87) PCT Pub. No.: WO2006/097029
PCT Pub. Date: Sep. 21, 2006

(65) Prior Publication Data
US 2008/0193434 A1 Aug. 14, 2008

(30) Foreign Application Priority Data
Mar. 15, 2005 (CN) .......................... 2005 1 0024393

(51) Int. Cl.
*C12Q 1/68* (2006.01)
*C12N 9/00* (2006.01)
*C12M 1/00* (2006.01)
*C23F 1/00* (2006.01)

(52) U.S. Cl.
USPC .............. 435/6.1; 435/183; 435/283.1; 216/3

(58) Field of Classification Search ............... 435/6, 6.1, 435/183, 283.1; 216/3
See application file for complete search history.

(56) References Cited

U.S. PATENT DOCUMENTS

| | | | | |
|---|---|---|---|---|
| 5,589,692 | A * | 12/1996 | Reed ................................ | 257/23 |
| 6,060,327 | A | 5/2000 | Keen | |
| 2006/0177482 | A1* | 8/2006 | Ding .............................. | 424/426 |
| 2006/0292081 | A1 | 12/2006 | Morton et al. | |

FOREIGN PATENT DOCUMENTS

| | | |
|---|---|---|
| CN | 1049115 | 2/2000 |
| CN | 1799629 | 7/2006 |
| DE | 198 52 543 | 5/2000 |
| JP | 2003-76036 | 3/2003 |

OTHER PUBLICATIONS

Substitute Specification and Preliminary Amendment filed with Co-Pending U.S. Appl. No. 11/813,265 on Jul. 2, 2007.
Co-Pending U.S. Appl. No. 12/002,888, filed Dec. 19, 2007.
Co-Pending U.S. Appl. No. 12/008,904, filed Jan. 15, 2008.
Fang et al, "The mechanisms of synergy of four drugs in protecting cortico-cerebral function from anoxic damage." Zhongguo Yingyong Shenglixue Zazhi, 12(3), 1996, p. 223-226. (Abstract provided).
Yu et al. "Self-Assembly Techniques for Fabrications of Nanocomposite Thin Films." Wuhan Ligong Daxue Xuebao • Xinxi Yu Guangligongcheng Ban, 24(4), 2002, p. 137-141. (Abstract provided).
Fang et al., Biomed & Pharmacother vol. 52 (1998) "Mode-actions of that Na(+)-Ca2+exchanger: from genes to mechanisms to a new strategy in brain disorders." pp. 145-56 Abstract Only.
International Search Report for international application No. PCT/CN2006/000108, dated May 18, 2006 (4 pages).
Written Opinion for international application No. PCT/CN2006/000108, dated May 18, 2006 (4 pages).

* cited by examiner

*Primary Examiner* — Robert T. Crow
(74) *Attorney, Agent, or Firm* — Hamre, Schumann, Mueller & Larson, P.C.

(57) ABSTRACT

A self-directed and self-assembled nanomedicine of quantized conductive junction and its preparation process are introduced. In the present disclosure, bio-organic medicine proteins are prepared into a quantized conductive junction with a nanostructure quantum dot and a polymer monolayer on an inorganic silicon surface by seven cooperative modes; and the preparation process of this inorganic-organic-biological hetero-polymer nano-structure component with free radical electrons, aromatic hetercycle structures, bio-fluorescence, and redox bioactivity is consist of making unitary, binary, ternary, and/or quaternary liquid biochemical medicines ingredients of an antioxidase antioxidant, a β-adrenergic receptor agonist, a $P_2$-purinergic receptor agonist, and/or a phenylalkylamine calcium channel blocker into a solid state quantized conductance junctions using $L_{16}(2)^{15}$ and $L_9(3)^4$ orthogonal protocol. Uses of self-directed and self-assembled nano-medicine molecules into quantized conductance junctions and its process cover quantum informatics, photoelectron nano-devices and nano-metrology.

11 Claims, 12 Drawing Sheets

US 8,431,338 B2

SELF-DIRECTING AND SELF-ASSEMBLING NANOMEDICINE INTO QUANTIZED CONDUCTANCE JUNCTIONS AND ITS PROCESS

RELATED APPLICATIONS

This application is the 35 U.S.C. §371 National Application of International Application No. PCT/CN06/000108, filed Jan. 23, 2006, which designated the United States, claiming priority to China Patent Application NO. 200510024393.0, filed 15 Mar. 2005.

TECHNOLOGY FIELD

This invention involves research fields of nanoscience and nanotechnology advanced materials, nanomedicine molecular quantum dots and monolayers as well as quantum information processors. It especially refers to nanomedicine self-directing and self-assembling into quantized conductance junctions and their preparation processes.

TECHNICAL BACKGROUND

Modern theories of BEC-BCS quantum physics, quantum chemistry, quantum biology and coordinating interaction quantum fields demonstrate that the massive bosons can be coherent at the lowest energy state of the same quantum state at a certain temperature for the $5^{th}$ state of mass-Bose-Einstein condensate (BEC); each electrons can respectively coupled into a Cooper pair and boson momentum coherence (BCS); an interaction of BEC-BCS enables each Fermions at different quantum states to be coupled into a Cooper pair that behaves like bosons and achieves the Fermion's coherence, such a Fermion's coherence presents quantized conductance switching phenomenon. The key point of realizing quantized conductance switching function is to hierarchically self-assemble quantized single electron tunneling junctions with nanometer architectures and, currently, it becomes a well-known research frontier worldwide. Self-directed and self-assembled technological method is a preparation process of foreign field-free at room temperature and in air to achieve hierarchically ordered quantized conductance junctions with nanometer structures and single electron tunneling. As reported elsewhere, inorganic-organic-biological polymers with hierarchically ordered cylinders-shaped nanometer architectures can be self-directed and self-assembled at the room temperature and in air. However, the construction of quantized conductance junctions with hierarchically ordered nanometer architectures and single electron tunneling does not involve. Albeit a quantized conductance atomic switch with 1 MHz frequency can operate at room temperature and in air, it does not satisfy 0-3000 Hz working frequencies of bioelectronics for generating bio-/chemo-electronic sensors. Even if inorganic molecules can be self-organized and grown at room temperature and in air into quantum dots and monolayers with nanometer architectures, they lack binary functions of recognizing targets and quantized conductance.

SUMMARY OF INVENTION

The aim of this invention is to provide products of nanomedicine self-directed and self-assembled into quantized conductance junctions.

The further goal is to offer preparation processes of biochemical pharmaceutical self-directing and self-assembling into quantized conductance junctions, quantum dots and monolayers, molecular wires with nanostructures and logic switching functions.

It is an advanced, novel and applicable preparation process that biochemical pharmaceuticals can self-direct and self-assemble into quantized conductance junctions, molecular wires, quantum dots and monolayers of nanomedicine with array configuration, nanometer size and logical switching function at room temperature and in air to bypass the bottleneck methods and technologies worldwide, based on the principle of Fermions' condensate. Up-to-date, there is not any report on biochemical pharmaceuticals self-directing and self-assembling into quantized conductance junctions, molecular wires, quantum dots and monolayers of nanomedicine with array configuration, nanometer size logical switching function.

The heart of this invention is nanomedicine self-directed and self-assembled into quantized conductance junctions to be used for developing molecular electronics or quantum devices, advanced photoelectron functional hybrid materials, hierarchically ordered nanometer architectures, drug delivery system and target-recognized functional quantum dot diagnostic tools and biochemical sensors.

The technological contents of this invention include preparation processes, self-assembly technological standards and metrological standards of quantized conductance junctions, monolayers and semiconductor quantum dots that are made by biochemical pharmaceutical building blocks with massively free electrons, aromatic structures and bioactive elements and oxidation-reduction (Redox) enzymatic polymers with nanometer structures and logical switching functions.

The invention employs coordinative interactions of Fermion's coherence and quantum field effects etc. to self-direct and self-assemble the unitary, binary, ternary and quaternary ultra-molecular systems of the antioxidase antioxidants, the agonist of the β-adrenergic receptors, the agonist of the $P_2$-purinergic receptors, and the antagonist of benzalkonium-typed calcium channels, which enable them to construct quantum dots and monolayers with array configuration nanometer structures and generate advanced materials with hybrid functions of quantized conductance junctions and nanomedicine through active photoelectrons in biochemical pharmaceuticals.

The self-directed and self-assembled method, as named in the invention, mainly refers to seven coordination modes to achieve self-directed and self-assembled quantum dots and monolayers of nanometer biochemical pharmaceutical molecular polymers with bioactive photoelectrons, valence electron flips or proton transferring π obits ($CH_2=CH-CH=CH_2$ and $-N=N-$ and/or non-bonding electron n orbits like -OH, $-NH_2$, -CL) or donors and receptors of single photon transferring (nitrogen aromatic structures and amino groups) as follows: (1) plain absorption on either the P— or the N-doped silicon chips via π electrons in aromatic structures; (2) tilted absorption on either the P— or the N-doped silicon chips via both of π electrons and un-paired electrons in nitrogen atoms; (3) vertical absorption on either the P— or the N-doped silicon chips via nitrogen atoms; (4) edged absorption on either the P— or the N-doped silicon chips via both of carbon and nitrogen atoms; (5) liquid absorption on either the P— or the N-doped silicon chips via OH-bonded tunneling junctions; (6) a layer-by-a layer self-assembly of silicon-based nanomedicine quantum dot hetero-structures via redox polymer thin films; (7) suspended hydrogen bonding formation on either the P— or the N-doped silicon chips via hydro-fluorine acids treating Si—$SiO_2$ metal surfaces; and the hetero-structures of inorganic silicon-organic pharmaceuticals-bioactive proteins finally construct as quantum dots, monolayers, and quantized conductance junctions.

The hetero-structural constituent of inorganic silicon-organic pharmaceuticals-bioactive proteins self-directing and self-assembling into quantum dots and monolayers with nanometer structures includes: 1) P— and N-doped Si (100)-$SiO_2$ core-shell layers; 2) active layers of massive hydrogen bonding; and 3) polymer layers of organic biochemical pharmaceutical proteins. The $3^{rd}$ layer employs constituents as follows: 1) safe food and drug agency (SFDA) standards-satisfied hydrochloride isoprenaline for intravenous injections (isoprenaline. HCl, 1 mg/2 ml); 2) SFDA standards-satisfied dry powders of adenosine triphosphate for intravenous injections (20 mg/2 ml); 3) SFDA standards-satisfied hydrochloride verapamil for intravenous injections (verapamil. HCl, 5 mg/2 ml); 4) SFDA/FDA standards-satisfied dry powders of superoxide dismutase; and 5) the optimum combinations thereof.

The self-directed and self-assembled preparation process standard is to arrange 0.5 cm$^2$ P— and N-doped Si—$SiO_2$ chips with massive hydrogen bonding into sterile 96-well cell plates with pre-prepared above organic biochemical pharmaceutical protein polymer solutions for 12 hours under the 10-class clean environments according to $L_{16}(2)^{15}$ and $L_9(3)^4$ orthogonal designs, washing surfaces with ion-free clean water 3 times and drying surfaces with nitrogen gas flows for characterizing topographic structures and current-voltage curve measurements by conducting tips and scanning probe microscopy (SPM) with atomic lateral resolution and micro-region scanning probe technology.

The optimum constituent of liquid self-directing and self-assembling silicon-based bioactive photoelectron organic biochemical pharmaceutical protein polymers into quantum dots and monolayers with nanometer structures are respectively described below.

1). There are 16 groups of self-directed and self-assembled technological processes on the P— and N-doped Si—$SiO_2$ chips respectively according to the $L_{16}(2)^{15}$ orthogonal design as follows:

(1) Adding 300 μl SFDA standard pharmaceutically physiological buffer solution (0.9% NaCl, 10 ml/packet) as the control.

(2) Using (1) as solvents, preparing $10^{-23}$M SFDA standard pharmaceutically hydrochloride verapamil solution, putting one molecule of the hydrochloride verapamil into the pre-set micro-well of sterile 96 well cell plate and maintaining the final volume of 300 μl.

(3) Using (1) as solvents, preparing $10^{-23}$M SFDA standard pharmaceutically hydrochloride isoprenaline solution, putting six molecules of the hydrochloride isoprenaline into the pre-set micro-well of sterile 96 well cell plate and maintaining the final volume of 300 μl.

(4) Using (1) as solvents, preparing $10^{-23}$M SFDA standard pharmaceutically superoxide dismutase solution, putting one molecule of the superoxide dismutase into the pre-set micro-well of sterile 96 well cell plate and maintaining the final volume of 300 μl.

(5) Using (1) as solvents, preparing $10^{-23}$M SFDA standard pharmaceutically adenosine triphosphate solution, putting four molecules of the adenosine triphosphate into the pre-set micro-well of sterile 96 well cell plate and maintaining the final volume of 300 μl.

(6) Respectively taking four molecules from the $10^{-23}$M SFDA standard pharmaceutically adenosine triphosphate solution and six molecules from the $10^{-23}$M SFDA standard pharmaceutically hydrochloride isoprenaline solution, then putting them into the pre-set micro-well of sterile 96 well cell plate and maintaining the final volume of 300 μl.

(7) Respectively taking one molecule from the $10^{-23}$M SFDA standard pharmaceutically hydrochloride verapamil solution and one molecule from the $10^{-23}$M SFDA standard pharmaceutically superoxide dismutase solution, then putting them into the pre-set micro-well of sterile 96 well cell plate and maintaining the final volume of 300 μl.

(8) Respectively taking one molecules from the $10^{-23}$M SFDA standard pharmaceutically hydrochloride verapamil solution and four molecules from the $10^{-23}$M SFDA standard pharmaceutically adenosine triphosphate solution, then putting them into the pre-set micro-well of sterile 96 well cell plate and maintaining the final volume of 300 μl.

(9) Respectively taking six molecules from the $10^{-23}$M SFDA standard pharmaceutically hydrochloride isoprenaline solution and one molecule from the $10^{-23}$M SFDA standard pharmaceutically superoxide dismutase solution, then putting them into the pre-set micro-well of sterile 96 well cell plate and maintaining the final volume of 300 μl.

(10) Respectively taking six molecules from the $10^{-23}$M SFDA standard pharmaceutically hydrochloride isoprenaline solution and four molecules from the $10^{-23}$M SFDA standard pharmaceutically adenosine triphosphate solution, then putting them into the pre-set micro-well of sterile 96 well cell plate and maintaining the final volume of 300 μl.

(11) Respectively taking one molecule from the $10^{-23}$M SFDA standard pharmaceutically superoxide dismutase solution and four molecules from the $10^{-23}$M SFDA standard pharmaceutically adenosine triphosphate solution, then putting them into the pre-set micro-well of sterile 96 well cell plate and maintaining the final volume of 300 μl.

(12) Respectively taking one molecule from the $10^{-23}$M SFDA standard pharmaceutically hydrochloride verapamil solution, four molecules from the $10^{-23}$M SFDA standard pharmaceutically hydrochloride isoprenaline solution and one molecule from the $10^{-23}$M SFDA standard pharmaceutically superoxide dismutase solution, then putting them into the pre-set micro-well of sterile 96 well cell plate and maintaining the final volume of 300 μl.

(13) Respectively taking one molecule from the $10^{-23}$M SFDA standard pharmaceutically hydrochloride verapamil solution, six molecules from the $10^{-23}$M SFDA standard pharmaceutically hydrochloride isoprenaline solution and four molecules from the $10^{-23}$M SFDA standard pharmaceutically adenosine triphosphate solution, then putting them into the pre-set micro-well of sterile 96 well cell plate and maintaining the final volume of 300 μl. (14) Respectively taking one molecule from the $10^{-23}$M SFDA standard pharmaceutically hydrochloride verapamil solution, one molecule from the $10^{-23}$M SFDA standard pharmaceutically superoxide dismutase solution and four molecules from the $10^{-23}$M SFDA standard pharmaceutically adenosine triphosphate solution, then putting them into the pre-set micro-well of sterile 96 well cell plate and maintaining the final volume of 300 μl.

(15) Respectively taking six molecules from the $10^{-23}$M SFDA standard pharmaceutically hydrochloride isoprenaline solution, one molecule from the $10^{-23}$M SFDA standard pharmaceutically superoxide dismutase solution and four molecules from the $10^{-23}$M SFDA standard pharmaceutically adenosine triphosphate solution, then putting them into the pre-set micro-well of sterile 96 well cell plate and maintaining the final volume of 300 μl.

(16) Respectively taking one molecule from the $10^{-23}$M SFDA standard pharmaceutically hydrochloride verapamil solution, six molecules from the $10^{-23}$M SFDA standard pharmaceutically hydrochloride isoprenaline solution, one molecule from the $10^{-23}$M SFDA standard pharmaceutically superoxide dismutase solution and four molecules from the $10^{-23}$M SFDA standard pharmaceutically adenosine triphosphate solution, then putting them into the pre-set micro-well of sterile 96 well cell plate and maintaining the final volume of 300 μl.

2) There are 9 groups of self-directed and self-assembled technological processes on the P— and N-doped Si—SiO2 chips respectively according to the $L_9(3)^4$ orthogonal design as follows:

(1) Respectively taking 100 molecules from the $10^{-23}$M SFDA standard pharmaceutically hydrochloride verapamil solution, 600 molecules from the $10^{-23}$M SFDA standard pharmaceutically hydrochloride isoprenaline solution, 100 molecules from the $10^{-23}$M SFDA standard pharmaceutically superoxide dismutase solution and 400 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 1200.

(2) Respectively taking 100 molecules form the $10^{-23}$M SFDA standard pharmaceutically hydrochloride verapamil solution, 1200 molecules from the $10^{-23}$M SFDA standard pharmaceutically hydrochloride isoprenaline solution, 200 molecules from the $10^{-23}$M SFDA standard pharmaceutically superoxide dismutase solution and 800 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2300.

(3) Respectively taking 100 molecules from the $10^{-23}$M SFDA standard pharmaceutically hydrochloride verapamil solution, 1800 molecules from the $10^{-23}$M SFDA standard pharmaceutically hydrochloride isoprenaline solution, 300 molecules from the $10^{-23}$M SFDA standard pharmaceutically superoxide dismutase solution and 1200 molecules from $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 3400.

(4) Respectively taking 200 molecules from $10^{-23}$M SFDA standard pharmaceutically hydrochloride verapamil solution, 600 molecules from the $10^{-23}$M SFDA standard pharmaceutically hydrochloride isoprenaline solution, 200 molecules from $10^{-23}$M SFDA standard pharmaceutically superoxide dismutase solution and 1200 molecules from $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2400.

(5) Respectively taking 200 molecules from the $10^{-23}$M SFDA standard pharmaceutically hydrochloride verapamil solution, 1200 molecules from $10^{-23}$M SFDA standard pharmaceutically hydrochloride isoprenaline solution, 300 molecules from the $10^{-23}$M SFDA standard pharmaceutically superoxide dismutase solution and 400 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2100.

(6) Respectively taking 200 molecules from the $10^{-23}$M SFDA standard pharmaceutically hydrochloride verapamil solution, 1800 molecules from the $10^{-23}$M SFDA standard pharmaceutically hydrochloride isoprenaline solution, 100 molecules from the $10^{-23}$M SFDA standard pharmaceutically superoxide dismutase solution and 800 molecules from the $10^{-23}$M SFDA standard pharmaceutically superoxide dismutase solution and 400 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2900.

(7) Respectively taking 300 molecules from the $10^{-23}$M SFDA standard pharmaceutically hydrochloride verapamil solution, 600 molecules from the $10^{-23}$M SFDA standard pharmaceutically hydrochloride isoprenaline solution, 300 molecules from the $10^{-23}$M SFDA standard pharmaceutically superoxide dismutase solution and 800 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2000.

(8) Respectively taking 300 molecules from the $10^{-23}$M SFDA standard pharmaceutically hydrochloride verapamil solution, 1200 molecules from the $10^{-23}$M SFDA standard pharmaceutically hydrochloride isoprenaline solution, 160 molecules from the $10^{-23}$M SFDA standard pharmaceutically superoxide dismutase solution and 1200 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2800.

(9) Respectively taking 300 molecules from the $10^{-23}$M SFDA standard pharmaceutically hydrochloride verapamil solution, 1800 molecules from the $10^{-23}$M SFDA standard pharmaceutically hydrochloride isoprenaline solution, 200 molecules from the $10^{-23}$M SFDA standard pharmaceutically superoxide dismutase solution and 400 molecules from the $10^{-23}$M SFDA standard pharmaceutically adenosine triphosphate solution, then putting them into the pre-set micro-well of sterile 96 well cell plate and maintaining the final volume of 300 μl. Finally, the total molecular number of four groups equals to 2700.

The invention employs modern BEC-BCS quantum physics, quantum chemistry, quantum biology, coordinative interaction quantum field theories and an interaction of inelastic electron tunneling to self-direct and self-assemble unitary, binary, ternary and quaternary polymers of isoprenaline, verapamil, superoxide dismutase and adenosine triphosphate with bioactive photoelectron properties, valence electron flipping or proton transferring π orbits ($CH_2=CH—CH=CH_2$ and $—N=N—$ and/or non-bonding electron n orbits like-OH, $—NH_2$, —CL) or donors and receptors of single photon transferring (nitrogen aromatic structures and amino groups) and enables all of them to construct quantum dots and monolayers with nanometer structures and binary functions of quantized conductance junctions and logic switching function at room temperature and in air. Such quantum biology and molecular interaction mechanisms-based methodology of self-directing and self-assembling quantum dots and monolayers into quantized conductance junctions with functional conversions and spatial geometrical configurations not only benefits drug discoveries with nanometer structures, but also profits self-directed and self-assembled functional hybrid advance materials with hierarchically ordered nanometer structures, molecular electronics or quantum devices, metrological standards of quantum biology, photoelectron information functional materials, target-recognized functional quantum dot diagnostic tools or bioelectronics chemical sensors made by monolayers with nanometer structures, etc.

The electrical metrological standard of quantized conductance junctions as stated in this invention refers to conducting atomic force microscopy (C-AFM) for characterizing topographic structures and electrical signals from single electron tunneling currents vs. a continuous pulse bias voltages (I-V) curves between the conducting tip and the sample. Conductance effects can be measured once bias voltages are less than the molecular threshold potentials; switching effects can be measured once bias voltages are larger than the molecular threshold potentials. An electrical metrological standard can be derived from the I-V non-linear measurements and analyses for characterizing electrical properties of quantized conductance junctions made by self-directed and self-assembled quantum dots and monolayers with nanometer structures, i.e., the I-V curves, the differential conductance spectrum (the $1^{st}$ derivative of the I-V curve), the inelastic electron interaction energy spectrum (the $2^{nd}$ derivative of the I-V curve), and time/frequency-energy spectrum (The faster Fourier Transformation of the differential conductance spectrum). The differential conductance spectrum contains threshold potential values that can be expressed by the central value of area calculation in the differential conductance spectrum, the maximum conductance peak that can be profiled by the height value of area calculation in the differential conductance spectrum; and Zeeman energy of electron spin momentum-related inelastic electron tunneling that can be read out by the absolute area value of the differential conductance spectrum. The time/frequency-energy spectrum includes central time/frequency that can be predicted by the central value of the time/frequency-energy spectrum area calculation; the lowest unoccupied molecular orbits /valence bands that can be estimated by the height of the time-energy spectrum; the highest occupied molecular orbits /conductance bands that can be evaluated by the height of the frequency-energy spectrum; the absolute value of Redox potentials due to intra-molecular charge transferring that can be expressed by the difference of the frequency-energy and time-energy spectra. It is difficult to acquire quantitative values as mentioned above from the classical quantum chemistry calculations. The typical attribute of quantized conductance junctions is sharp peaks near the zero bias potential in the differential conductance spectrum (a typical quantum mechanical resonance Kondo effect). The behavior of negative differential conductance/resistance junction refers to tunneling currents is declining when bias potentials is elevating, which is the basis of a resonance tunneling diode and simple memory devices. Metal-like vertical linear resistance in I-V curves shows the electrical property of superconductors. The electrical. behavior of Josephson junctions refers to vertical linear resistance plus parallel linear insulator properties in the I-V curves. The electrical behavior of semiconductors refers to the presence of positive and negative tunneling currents across the zero bias potential. Non-thermodynamic energy-driven phase transition velocity uncertain quantum waves or zero-point motions imply the presence of a unitary wave around the zero point of the time/frequency-energy spectrum whereas the presence of non-unitary waves around the zero point of the time/frequency-energy spectrum shows thermodynamic energy-driven phase transition velocity certain quantum waves or non-zero-point motion. The phase transition velocity depends on the self-autocorrelation functions of phase factors, which can be calculated by the central value of the time-energy spectrum multiplying the central value of frequency-energy spectrum.

The invention employs $L_{16}(2)^{15}$ and $L_9(3)^4$ orthogonal optimum methods, self-directed and self-assembled coordination modes, scanning probe microscopy and non-linear analysis of I-V parameters and its auto-correlation functions calculations to acquire zero-point motion and non-zero-point motion electrical properties of quantized conductance junctions, superconductor junctions, negative differential conductance/resistance junctions, Josephson junctions with binary characteristics of highly efficient protection of cardiopulmonary cerebral vascular system from hypoxic injuries and bioactive photoelectron nanomedicines, these electrical properties reflect attributes of electrical metrology triangle of single electron tunneling, quantized conductance and Josephson effect at the quantum level standard. The key point of the technological method of invention is to acquire the consistency of single electron tunneling, quantized conductance and Josephson effect in the triangle electrical metrological standard.

The typically electrical property of this invention is to develop the basis of hierarchically ordered nanostructures self-directing and self-assembling into functional hybrid advanced materials, molecular electronics or quantum devices, metrological standards of quantum biology, photoelectron information materials, target-recognized functional quantum dot diagnostic tools and/or biochemo-sensors with nanostructure monolayers. The key constituent of quantized conductance junctions with nanostructures and monolayers includes the unitary, binary, ternary and quaternary self-directing and self-assembling system of isoprenaline, verapamil, superoxide dismutase and adenosine triphosphate:

Where the optimum preparation process of the unitary self-directed and self-assembled quantized conductance junctions with nanostructures and monolayers contains the molar ratio of 1:0:0:0; 0:1:0:0; 0:0:1:0; 0:0:0:1.

Where the optimum preparation process of the binary self-directed and self-assembled quantized conductance junctions with nanostructures and monolayers contains the molar ratio of 1:1:0:0; 1:0:1:0; 1:0:0:1; 0:1:1:0; 0:1:0:1; 0:0:1:1.

Where the optimum preparation process of the ternary self-directed and self-assembled quantized conductance junctions with nanostructures and monolayers contains the molar ratio of 1:1:1:0; 1:0:1:1; 1:1:0:1; 0:1:1:1.

Where the optimum preparation process of the quaternary self-directed and self-assembled quantized conductance junctions with nanostructures and monolayers contains the ratio of 1:1:1:1; 1:2:2:2; 1:3:3:3; 2:1:2:3; 2:2:3:1; 2:3:1:2; 3:1:3:2; 3:2:1:3; 3:3:2:1.

The analysis results of I-V curves, the $1^{st}$ and the $2^{nd}$ derivatives of the I-V curves and the time/frequency-energy spectra in the above unitary, binary, ternary and quaternary and different quaternary self-directing and self-assembling systems reveal 25 groups of array data and 25 different sizes of nanomedicine constructing quantized conductance junction matrices with nanostructures or and monolayers on the P— and N-doped $Si$—$SiO_2$ chips. The thickness of quantized conductance junction matrices with nanostructures quantum dots is controllable, for examples, the Josephson junctions with the thickness 440 Å, 260 Å, 42 Å and 17 Å, and the quantized conductance junctions with the thickness 70 Å and 60 Å; The size of quantized conductance junctions with monolayers is also controllable, for instances, the Josephson junction arrays with the thickness 190 Å, 100 Å, 42 Å, 34 Å and 18 Å; the superconductor junction arrays with the thickness 70 Å and 85 Å; the negative differential conductance/resistance junctions arrays with the thickness 400 Å, 55 Å, 42 Å, 36 Å, 23 Å, 21 Å and 14 Å; the zero-point motion-typed quantized conductance junction arrays with the thickness 32

Å, 28 Å, 26 Å, 22 Å, 20 Å, 19 Å, 15 Å and 11.5 Å; the non-zero-point motion-typed quantized conductance junction arrays with the thickness 70 Å, 55 Åand 30 Å; the complex quantized conductance junction(Josephson junctions plus negative differential conductance/resistance junctions) arrays with the thickness 16 Å.

The range of phase factors for the mentioned non-zero-point motion-typed quantized conductance junctions with monolayers covers the square 49, 39 and 147 Hz/s. The self-directed and self-assembled quantized conductance junctions with bioactive photoelectron nanomedicine show array configuration, their sizes are controllable, and there are multiple topographic structures and electrical properties. The invention not only benefits inventions of self-directed and self-assembled hybrid advanced materials with hierarchically ordered nanostructures, molecular electronics or quantum devices, metrological standards of quantum biology, photoelectron information functional materials, target-recognized functional quantum dot diagnostic tools, and bio-chemo-electronic-sensors with nanometer structural mono-layers, but also profits drug delivery system and drug discoveries targeting to disease mechanisms.

The preparation process of self-directed and self-assembled nanomedicine quantized conductance junctions with bioactive photoelectrons, quantum dots and monolayers with nanostructures covers following methods and steps.

Preparing pharmaceutical solutions according to pharmaceutical standards issued by the ministry of health in China:

1. Preparing hydrochloride verapamil solution
2. Preparing hydrochloride isoprenaline solution
3. Preparing superoxide dismutase in physiological buffer solution
4. Preparing adenosine triphosphate in physiological buffer solution
5. Taking the optimum molecular numbers from each constituent at the range of $10^{-23}$M, mixing them at room temperature, adding physiological buffer to 300 μl and keeping at −4° C. for applications.
6. Employing process standards of semiconductor industry to clean silicon surface and activated surface with hydrofluorine acids, preparing the P— and N-doped Si (100)-$SiO_2$chips with massively suspended hydrogen bonding as the substrates of self-directed and self-assembled quantum dots and mono-layers. Under the class 10 clean environments immersing the clean P— and N-doped Si(100)-$SiO_2$chips with massively suspended hydrogen bonding in the unitary, binary, ternary and quaternary pharmaceutical solutions for 12 hours according to the $L_{16}(2)^{15}$ and the $L_9(3)^4$ orthogonal optimum design, cleaning three times with de-ionized sterile water, drying the silicon surface with nitrogen gas for characterizations by the conducting atomic force microscopy(C-AFM).

DESCRIPTION OF DRAWINGS

FIG. 1. The C-AFM image quantized Josephson junction's topographic structure.

FIG. 8a-d cover four threshold potential values: 8.24V, −7.96V, 0.4V, −0.84V; the maximum conductance data: −56.346787 pA/V, 31.47083 pA/V, −0.52083 pA/V, 49.07188 pA/V; and the absolute valued of Zeeman free energy relevant to the electron spin momentum-based inelastic electron tunneling charge transferring reaction: |−4.68425|eV, |6.72075|eV, |0.00342|eV, and |−3.35375|eV.

DETAILED EXAMPLES

Example 1

Figure 1A:
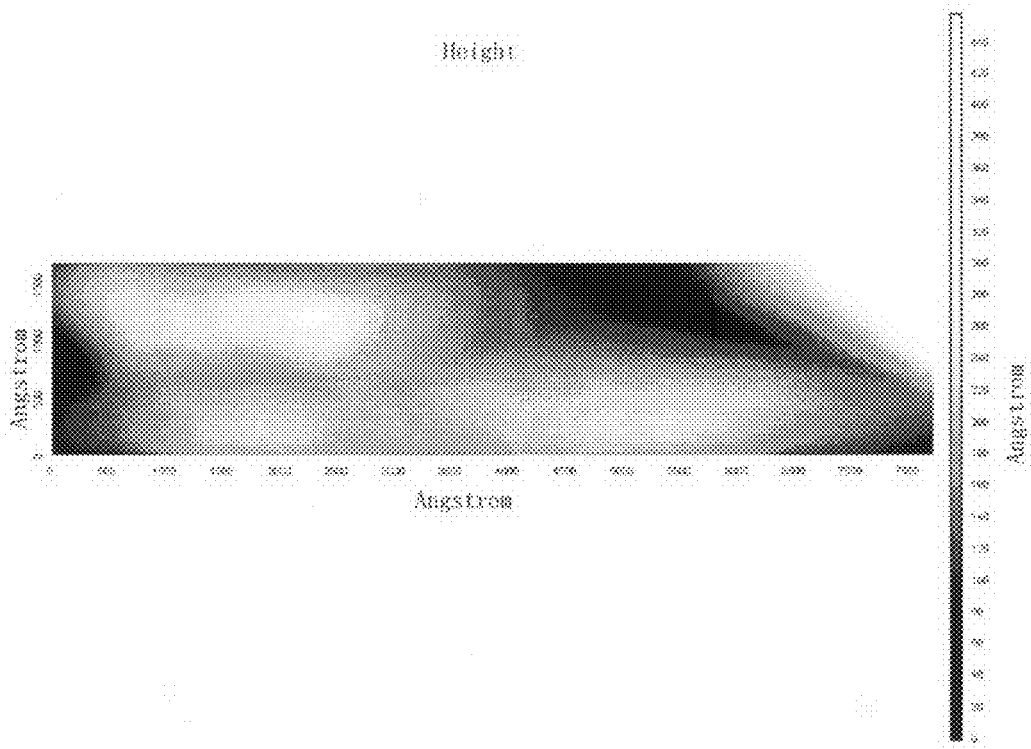
FIG. 1a is the C-AFM topographic structure image of the quantum dot and the Josephson junction with a larger size nanostructures up to 440 Å.
Figure 1B:
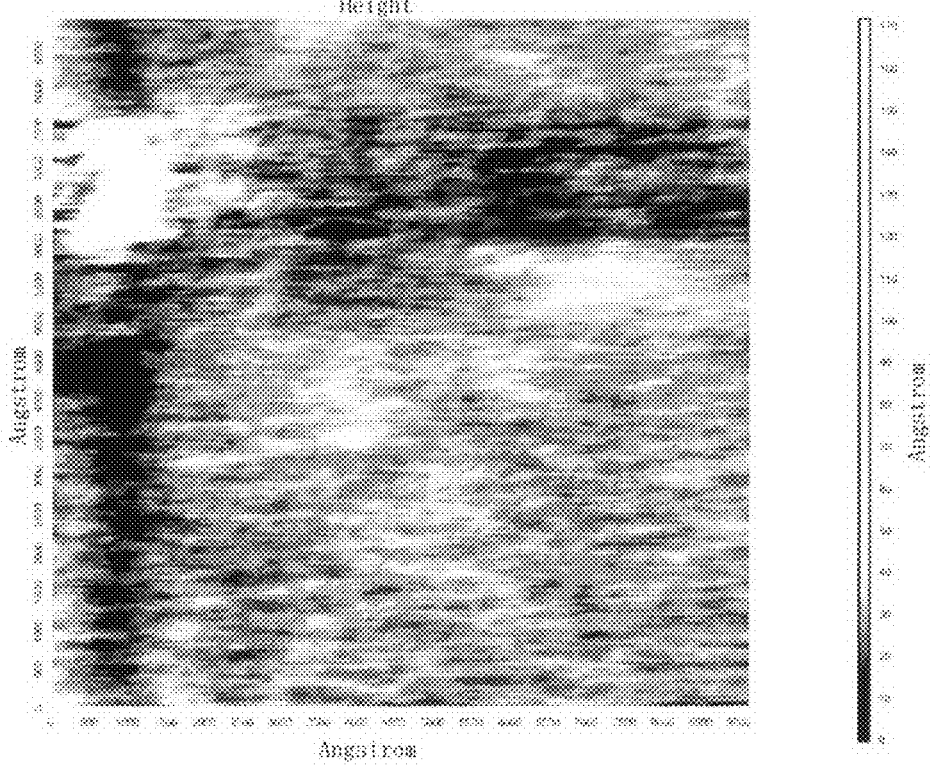
FIG. 1b is the C-AFM topographic structure image of the quantized Josephson junction with logical switching function and the thickness 85 Å quaternary nanomedicine monolayer nanostructures.
Figure 2A:
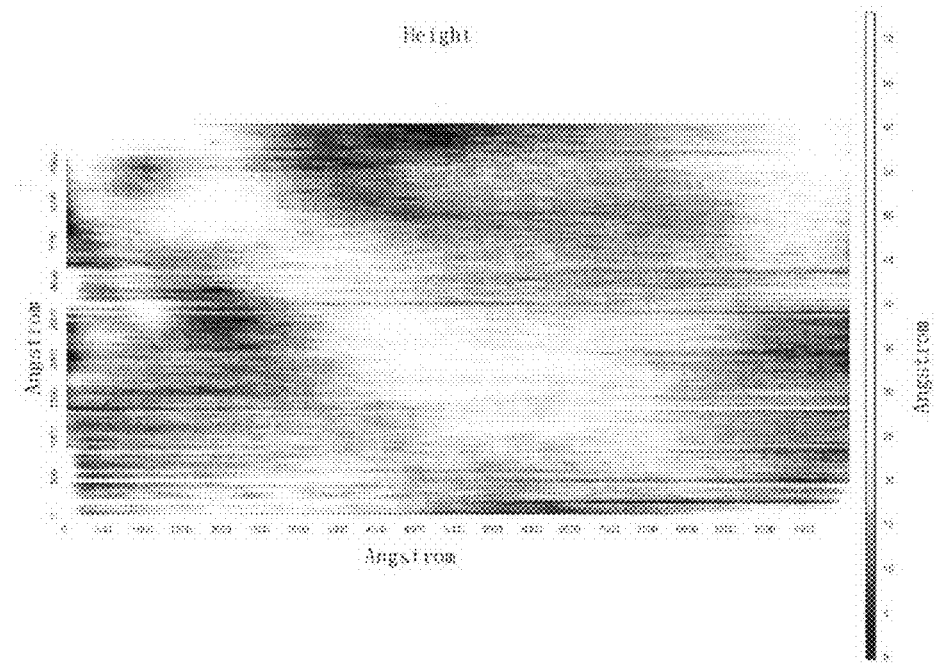
FIG. 2a-b. The C-AFM image topographic structures of monolayers and quantized superconductor junctions with ternary and quaternary pharmaceutical molecules at the thickness 70 Å and 85 Å respectively.
Figure 2B:
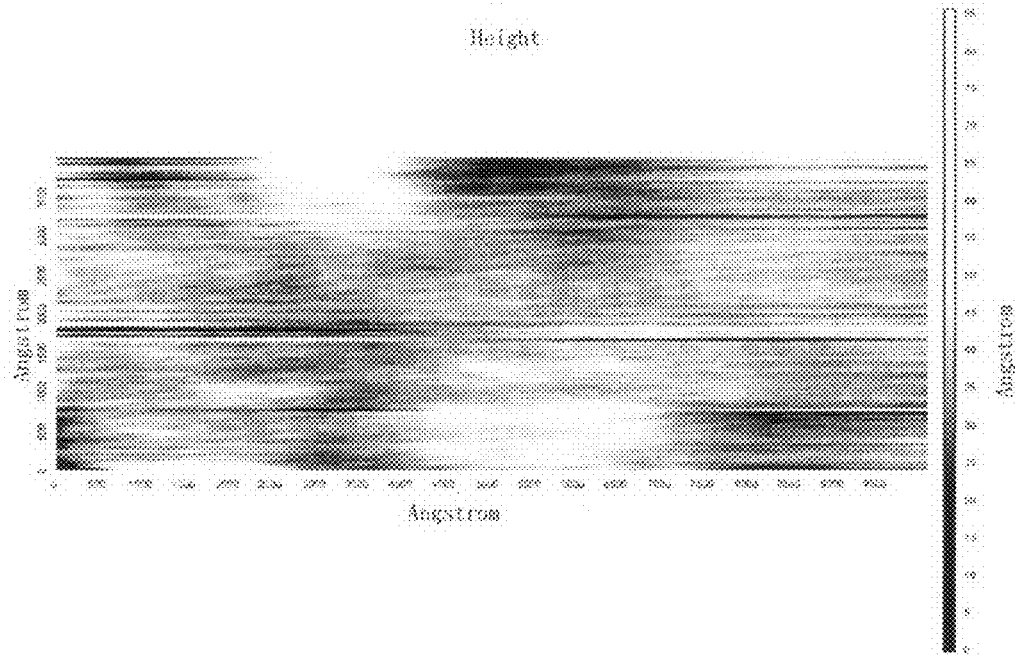
Figure 3:
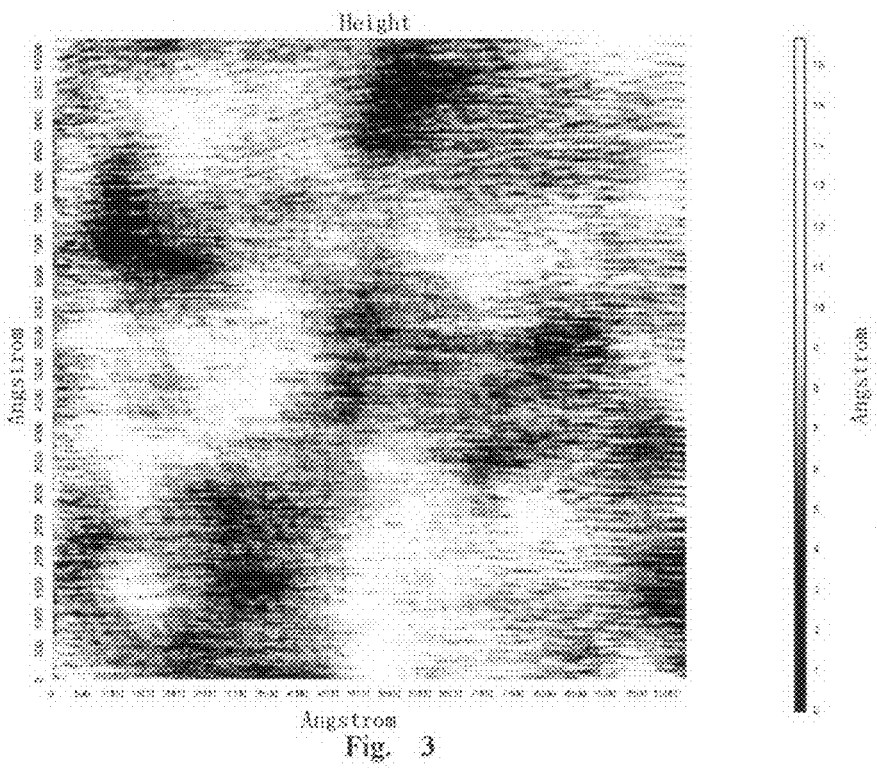
FIG. 3. The C-AFM image topographic structures of the complex quantized junction (Josephson junction plus negative differential conductance/resistance junction) with the quaternary pharmaceutical molecule monolayer at the thickness 16 Å.
Figure 4:
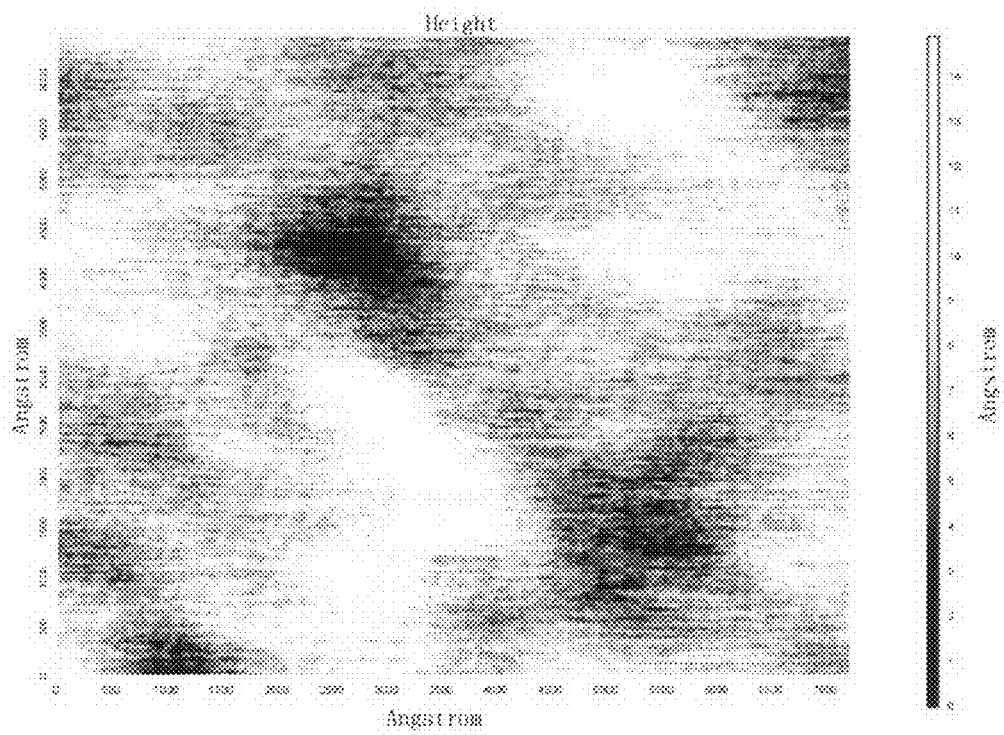
FIG. 4. The C-AFM image topographic structures of the quantized negative differential conductance/resistance junction with logical switching function made by the unitary pharmaceutical monolayer at the thickness 14 Å.

Preparing pharmaceutical solutions according to the pharmaceutical standards issued by the ministry of health in china as follows:

1. Preparing hydrochloride verapamil solution in the packet of 2.5 mg/5 ml.
2. Preparing hydrochloride isoprenaline solution in the packet of 2 mg/100 ml
3. Preparing physiological buffer superoxide dismutase solution in the packet of 1 mg/2 ml 4. Preparing physiological buffer adenosine triphosphate solution in the packet of 20 mg/3.3 ml 5. Respectively preparing the $10^{-23}$ M physiological buffer solutions of the 1-4 solutions 6. Respectively taking each pharmaceutical molecular numbers from the $10^{-23}$ M physiological buffer solutions according to the ratio of 1:3:2:1, mixing them at room temperature, adding physiological buffer solution up to 300 μl and keeping at −4° C. for applications 7. Employing semiconductor industry standards of cleaning silicon chip's surfaces and activating surfaces with hydrofluorine acids, preparing the P— and N-doped Si(100)-SiO$_2$ chips with massive hydrogen bonding as the substrates of self-directed and self-assembled quantum dots and monolayers. Under the class 10 clean environments, immersing the activated Si-chips into the optimum unitary, binary, ternary and quaternary pharmaceutical solutions for 12 hours according to the $L_{16}(2)^{15}$ and the $L_9(3)^4$, cleaning the surface three times with de-ionized sterile water, and drying the surface with nitrogen gas for characterizing by the C-AFM. The FIG. 1$b$ shows the C-AFM topographic structure image; the FIG. 7$a$ profiles the I-V curves of the complex quantized conductance junction (Josephson junction plus negative differential conductance/resistance junction); the FIG. 8$a$ is the differential conductance spectrum derived from the FIG. 7$a$, where covers the value of 8.24V threshold potential, the maximum conductance value of −56.346787 pA/V and the absolute value of Zeeman free energy |−4.68425|eV that is relevant to electron spin momentum, inelastic electron tunneling and charge transferring reactions; the FIG. 9$a$-$b$ reveals frequency/time-energy spectra, where the central frequency/time value 48.82813 Hz/48.82813 s that can be acquired from the central value of the area calculation in the frequency/time-energy spectra after the faster Fourier transformation of FIG. 8$a$, the highest occupied molecular orbit (HOMO)/conductance band(CB) value 0.00316 eV and the lowest unoccupied molecular orbit(LUMO)/valence band(VB) value 7.91144 E-4 eV that can be respectively acquired from the height values of the area calculation in the frequency-energy spectrum and time-energy spectrum after the faster Fourier transformation of FIG. 8$a$, and the absolute value of oxidative potential difference (0.15578−0.03895=0.11783 eV) that can be read out from the area difference between the frequency-energy spectrum and time-energy spectrum after the faster Fourier transformation of FIG. 8$a$.

Example 2

Preparing pharmaceutical solutions according to the pharmaceutical standards issued by the ministry of health in china as follows:

1. Preparing hydrochloride verapamil solution in the packet of 2.5 mg/5 ml.

2. Preparing hydrochloride isoprenaline solution in the packet of 2 mg/100 ml

3. Preparing physiological buffer superoxide dismutase solution in the packet of 1 mg/2 ml 4. Preparing physiological buffer adenosine triphosphate solution in the packet of 20 mg/3.3 ml 5. Respectively preparing the $10^{-23}$ M physiological buffer solutions of the 1-4 solutions 6. Respectively taking each pharmaceutical molecular numbers from the $10^{-23}$ M physiological buffer solutions according to the ratio of 0:1:0:0, mixing them at room temperature, adding physiological buffer solution up to 300 μl and keeping at −4° C. for applications 7. Employing semiconductor industry standards of cleaning silicon chip's surfaces and activating surfaces with hydrofluorine acids, preparing the P— and N-doped Si(100)-SiO$_2$ chips with massive hydrogen bonding as the substrates of self-directed and self-assembled quantum dots and monolayers. Under the class 10 clean environments, immersing the activated Si-chips into the optimum unitary, binary, ternary and quaternary pharmaceutical solutions for 12 hours according to the $L_{16}(2)^{15}$ and the $L_9(3)^4$, cleaning the surface three times with de-ionized sterile water, and drying the surface with nitrogen gas for characterizing by the C-AFM. The FIG. 1$a$ shows the C-AFM topographic structure image; the FIG. 7$b$ profiles the I-V curves of the quantized negative differential conductance junction; the FIG. 8$b$ is the differential conductance spectrum derived from the FIG. 7$b$, where covers the value of −7.96V threshold potential, the maximum conductance value of 31.47083 pA/V and the absolute value of Zeeman free energy |6.72075|eV that is relevant to electron spin momentum, inelastic electron tunneling and charge transferring reactions; the FIG. 9$c$-$d$ reveals frequency/time-energy spectra, where the central frequency/time value 39.0625 Hz/39.06254 s that can be acquired from the central value of the area calculation in the frequency/time-energy spectra after the faster Fourier transformation of FIG. 8$b$, the highest occupied molecular orbit (HOMO)/conductance band(CB) value 5.80645 E-4 eV and the lowest unoccupied molecular orbit(LUMO)/valence band(VB) value 1.45161 E-4 eV that can be respectively acquired from the height values of the area calculation in the frequency-energy spectrum and time-energy spectrum after the faster Fourier transformation of FIG. 8$b$, and the absolute value of oxidative potential difference (0.06358−0.0159=0.0468 eV) that can be read out from the area difference between the frequency-energy spectrum and time-energy spectrum after the faster Fourier transformation of FIG. 8$b$.

Example 3

Preparing pharmaceutical solutions according to the pharmaceutical standards issued by the ministry of health in china as follows:

1. Preparing hydrochloride verapamil solution in the packet of 2.5 mg/5 ml.

Figure 5:
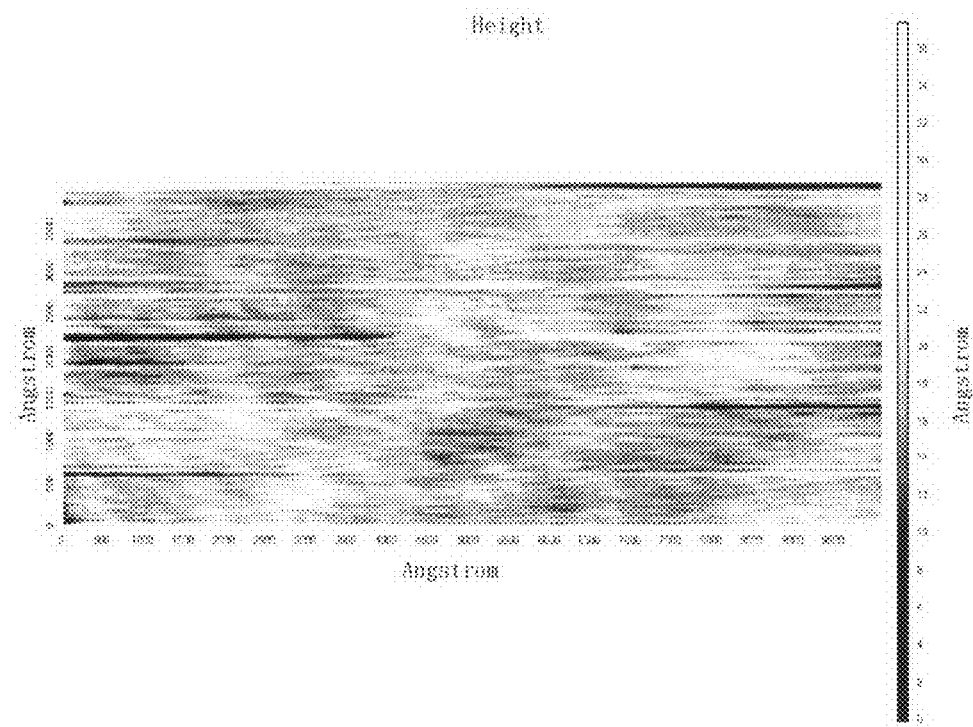
FIG. 5. The C-AFM image topographic structures of the quantized semiconductor junction with logical switching function made by the ternary pharmaceutical molecular monolayer nanostructures at the thickness 11.5 Å.
Figure 8A:
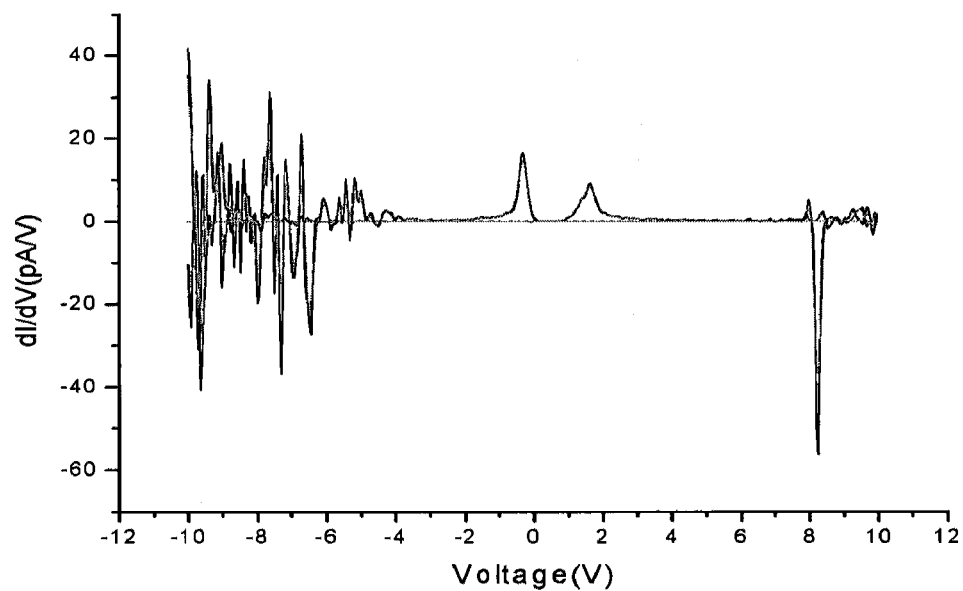
FIG. 8a-d. The differential conductance spectra correspond to the FIG. 7a-d.
Figure 8B:
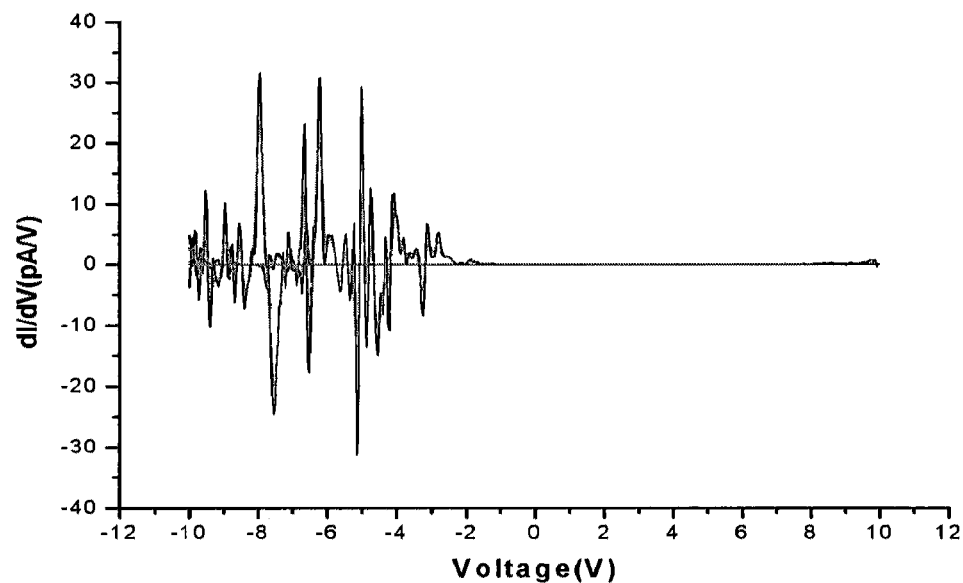
Figure 8C:
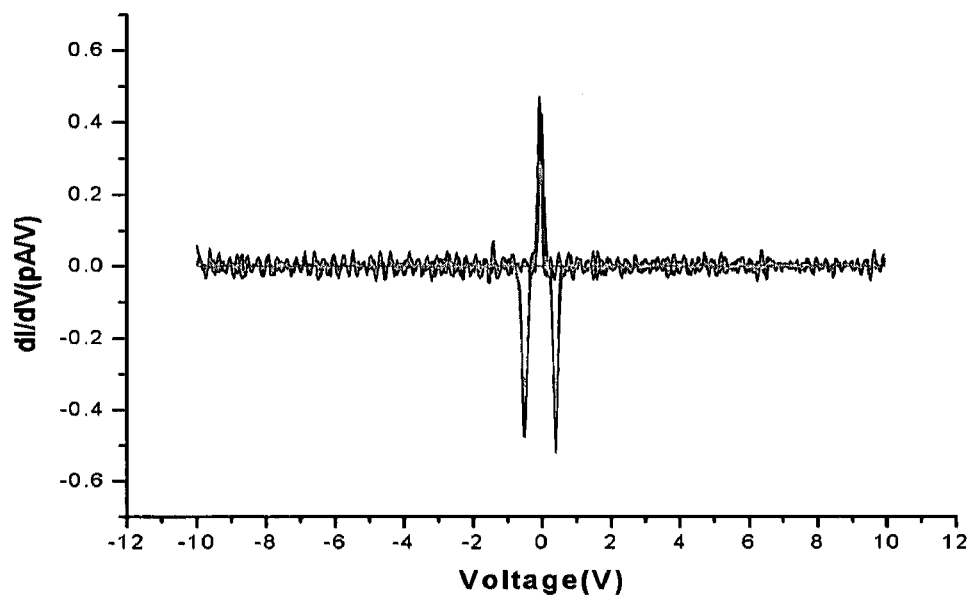

2. Preparing hydrochloride isoprenaline solution in the packet of 2 mg/100 ml 3. Preparing physiological buffer superoxide dismutase solution in the packet of 1 mg/2 ml 4. Preparing physiological buffer adenosine triphosphate solution in the packet of 20 mg/3.3 ml 5. Respectively preparing the $10^{-23}$ M physiological buffer solutions of the 1-4 solutions 6. Respectively taking each pharmaceutical molecular numbers from the $10^{-23}$ M physiological buffer solutions according to the ratio of 1:0:1:1, mixing them at room temperature, adding physiological buffer solution up to 300 μl and keeping at −4° C. for applications 7. Employing semiconductor industry standards of cleaning silicon chip's surfaces and activating surfaces with hydrofluorine acids, preparing the P— and N-doped Si(100)-SiO$_2$ chips with massive hydrogen bonding as the substrates of self-directed and self-assembled quantum dots and monolayers. Under the class 10 clean environments, immersing the activated Si-chips into the optimum unitary, binary, ternary and quaternary pharmaceutical solutions for 12 hours according to the $L_{16}(2)^{15}$ and the $L_9(3)^4$, cleaning the surface three times with de-ionized sterile water, and drying the surface with nitrogen gas for characterizing by the C-AFM. The FIG. 5 shows the C-AFM topographic structure image; the FIG. 7$c$ profiles the I-V curves of the quantized superconductor conductance junction; the FIG. 8c is the differential conductance spectrum derived from the FIG. 7c, where covers the value of 0.4V threshold potential, the maximum conductance value of −0.52083 pA/V and the absolute value of Zeeman free energy |0.00342|eV that is relevant to electron spin momentum, inelastic electron tunneling and charge transferring reactions; the FIG. 9e-f reveals frequency/time-energy spectra, where the central frequency/time value −146.48438 Hz/−146.48438 s that can be acquired from the central value of the area calculation in the frequency/time-energy spectra after the faster Fourier transformation of FIG. 8c, the highest occupied molecular orbit (HOMO)/conductance band(CB) value 1.61372 E-7 eV and the lowest unoccupied molecular orbit (LUMO)/valence band(VB) value 4.0343 E-8 eV that can be respectively acquired from the height values of the area calculation in the frequency-energy spectrum and time-energy spectrum after the faster Fourier transformation of FIG. 8c, and the absolute value of oxidative potential difference (1.008388 E-5−2.5097 E-6=7.57418 E-6 eV) that can be read out from the area difference between the frequency-energy spectrum and time-energy spectrum after the faster Fourier transformation of FIG. 8c.

Example 4

Figure 6:
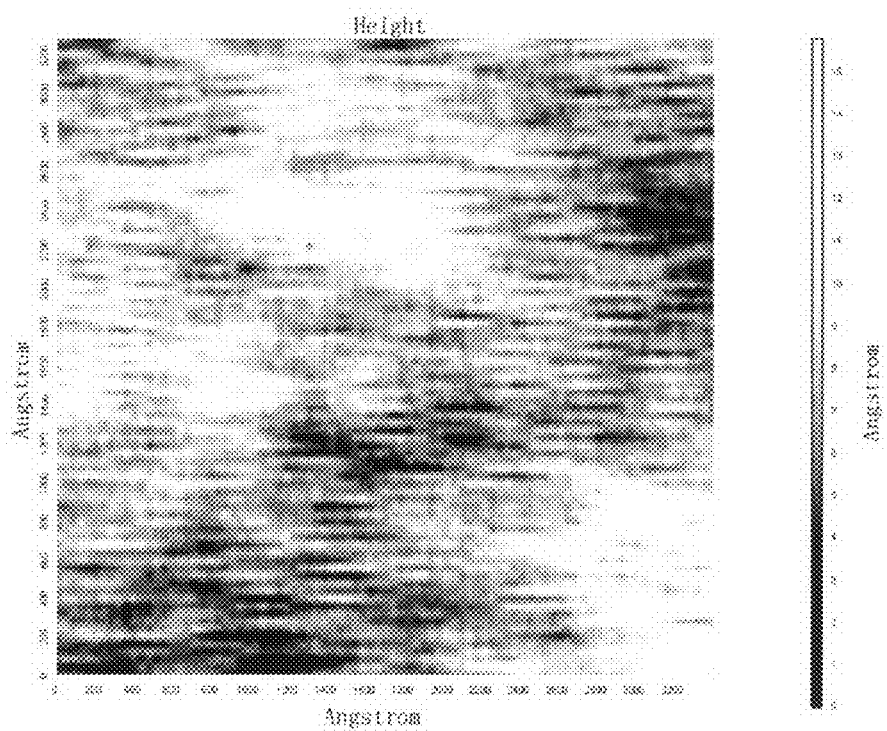
FIG. 6. The C-AFM image topographic structures of the quantized semiconductor junction with logical switching function made by the binary pharmaceutical molecular monolayer at the thickness 15 Å nanostructures.
Figure 7A:
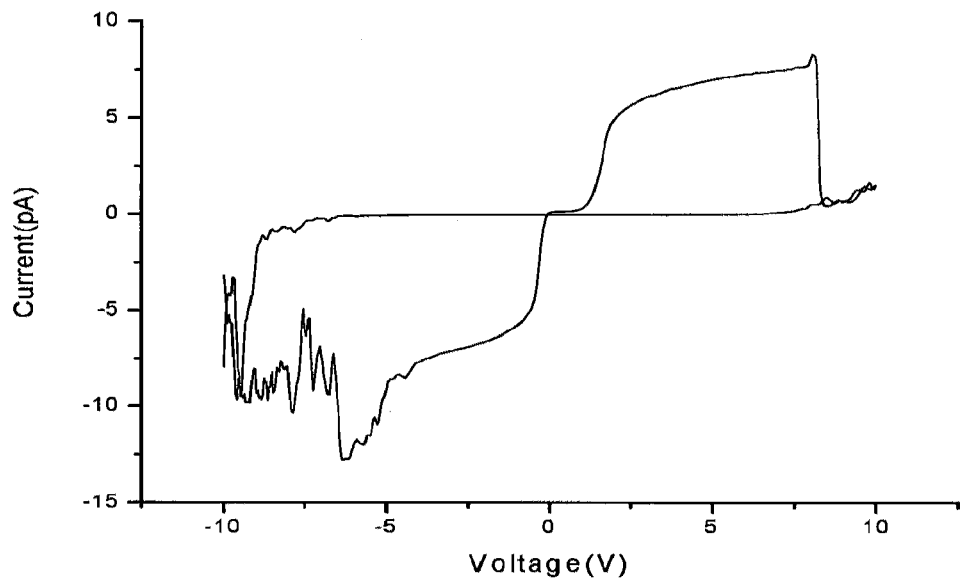
FIG. 7a-d. The C-AFM I-V curve spectrum of the quantized complex junction (Josephson junction plus negative differential conductance/resistance junction), the negative differential conductance/resistance junction, the quantized superconductor junction and the quantized semiconductor junction.
Figure 7B:
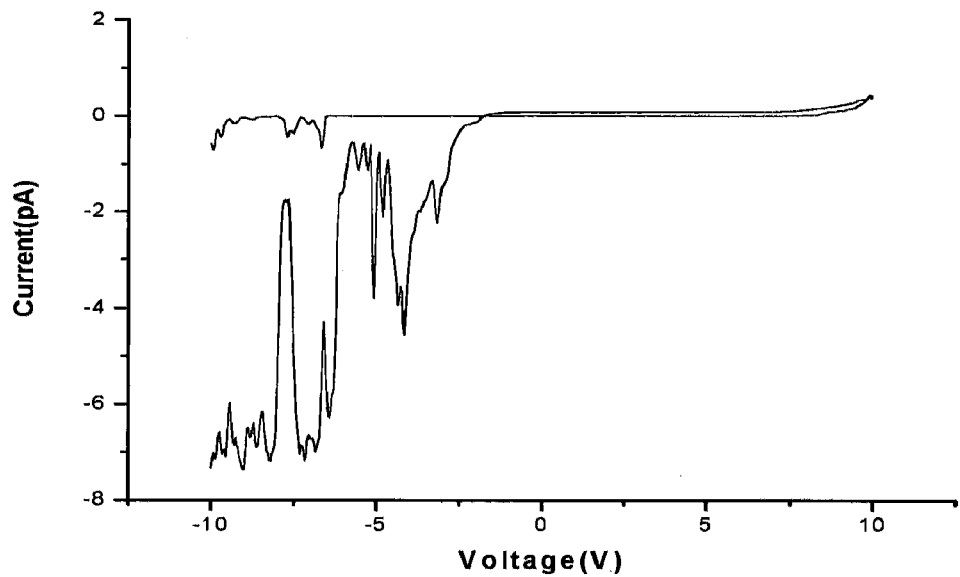
Figure 7C:
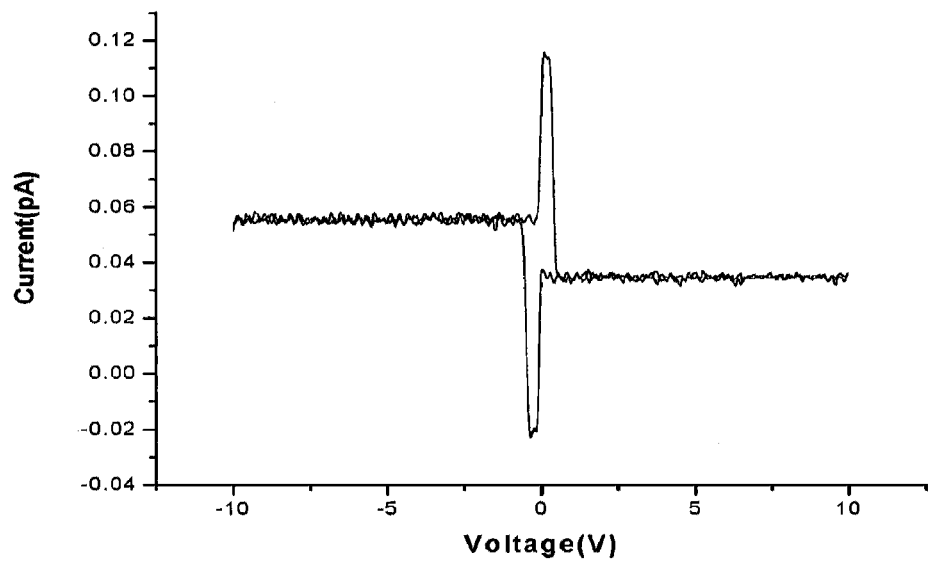
Figure 7D:
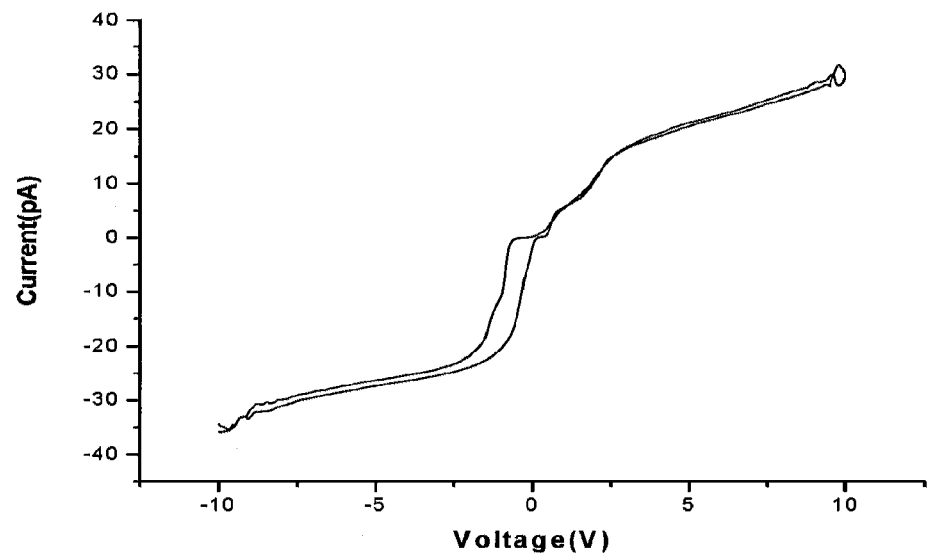
Figure 8D:
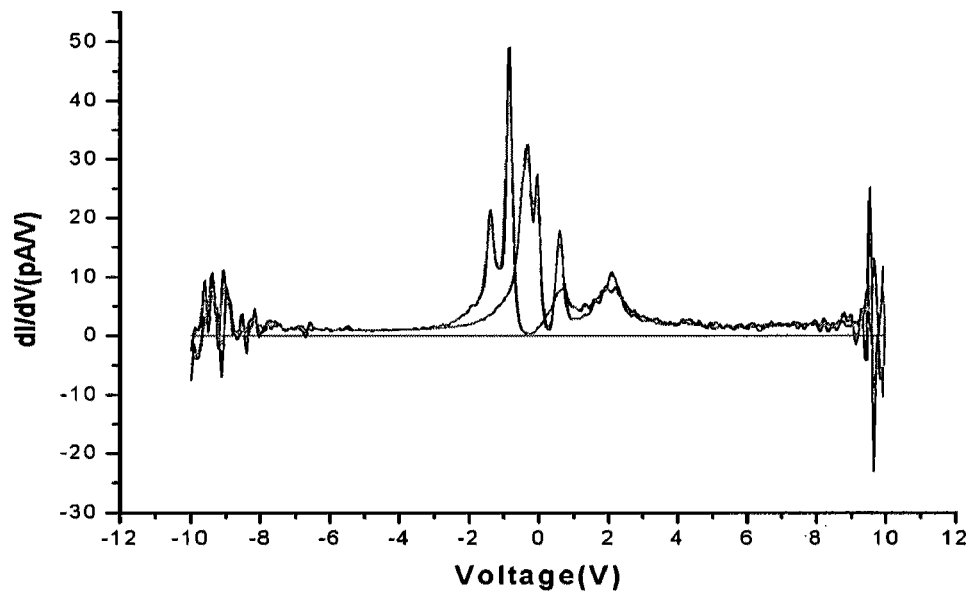
Figure 9A:
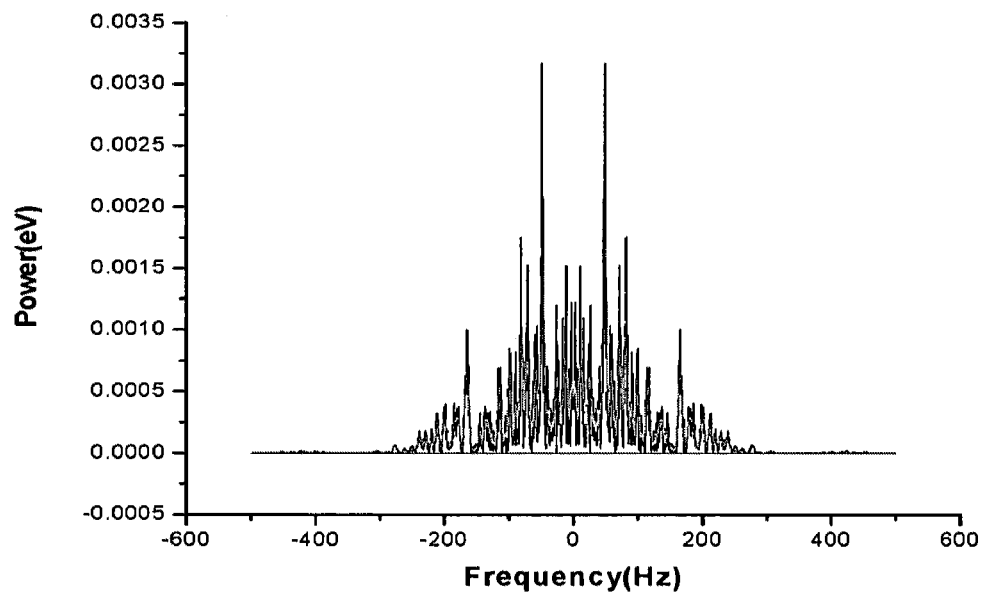
FIG. 9a-h. The frequency/time-energy spectra correspond to faster Fourier transformation of the FIG. 8a-d. Wherein there are four parental data of central frequency and central time: 48.82813 Hz/48.82813 s, 39.0625 Hz/39.0625 s, −146.48438 Hz/−146.48438 s, and zero Hz/s, respectively acquiring from the central values in the area calculation of FIG. 8a-d differential conductance spectra; four parental data of the lowest unoccupied molecular orbits/valence bands (7.91144 E-4 eV, 1.45161 E-4 eV, 4.0343 E-8 eV, and 0.00976 eV) and the highest occupied molecular orbits/conductance bands (0.00316 eV, 5.80645 E-4 eV, 1.61372 E-7 eV, and 0.03905 eV), respectively acquiring from the height values of the area calculation in the FIG. 8a-d time-energy and frequency-energy spectra; and four parental data of oxidative potentials: 0.15578-0.03895=0.11783 eV, 0.06358-0.0159=0.0468 eV, 1.008388 E-5−2.5097 E-6=7.57418 E-6 eV, and 0.13851−0.03463=0.10498 eV, respectively acquiring from the differences between the frequency-energy spectrum and the time-energy spectrum of the FIG. 8a-d differential conductance spectra.
Figure 9B:
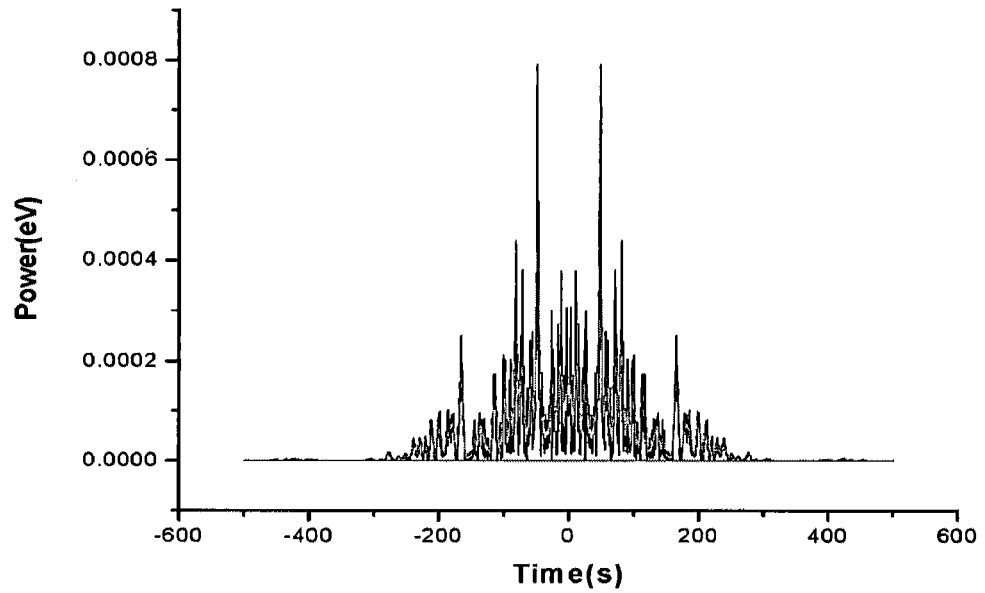
Figure 9C:
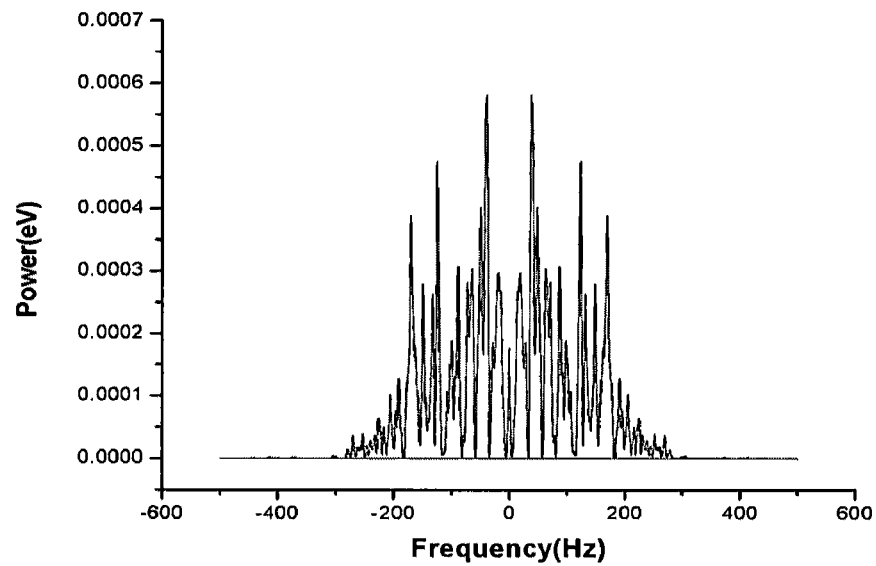
Figure 9D:
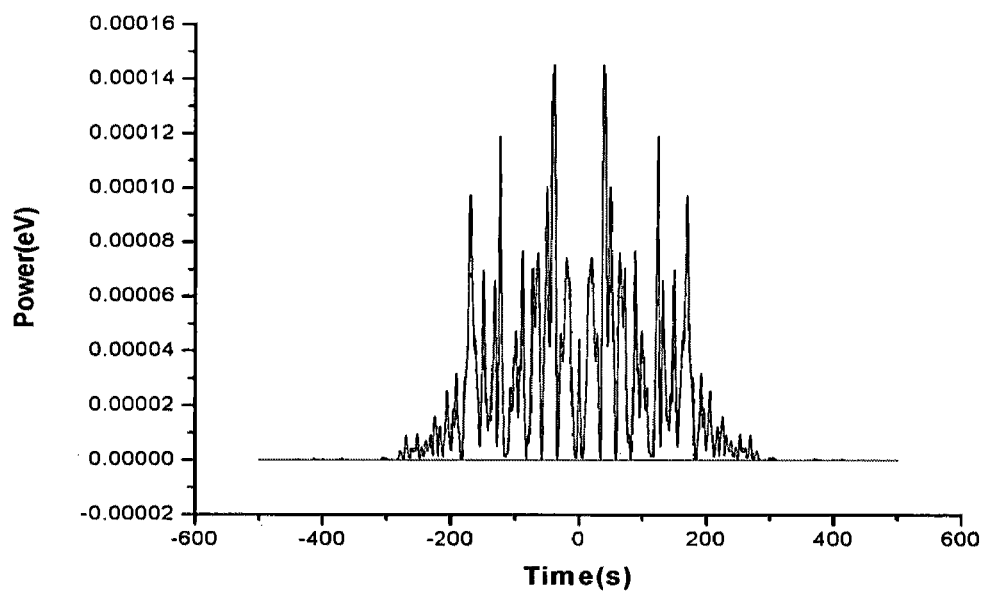
Figure 9E:
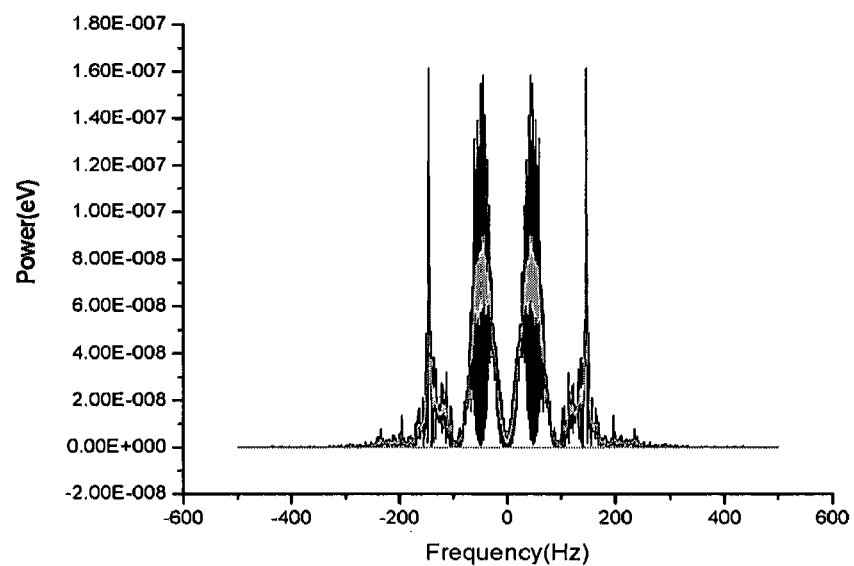
Figure 9F:
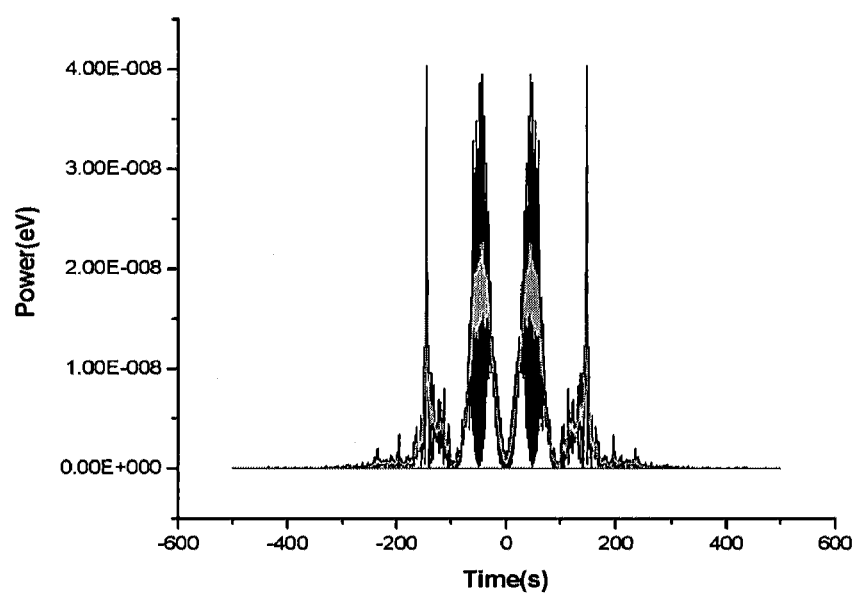
Figure 9G:
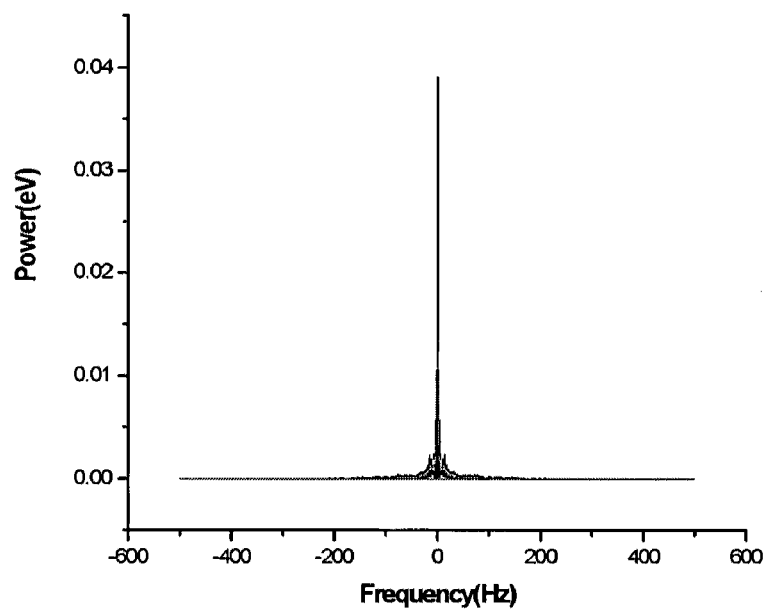
Figure 9H:
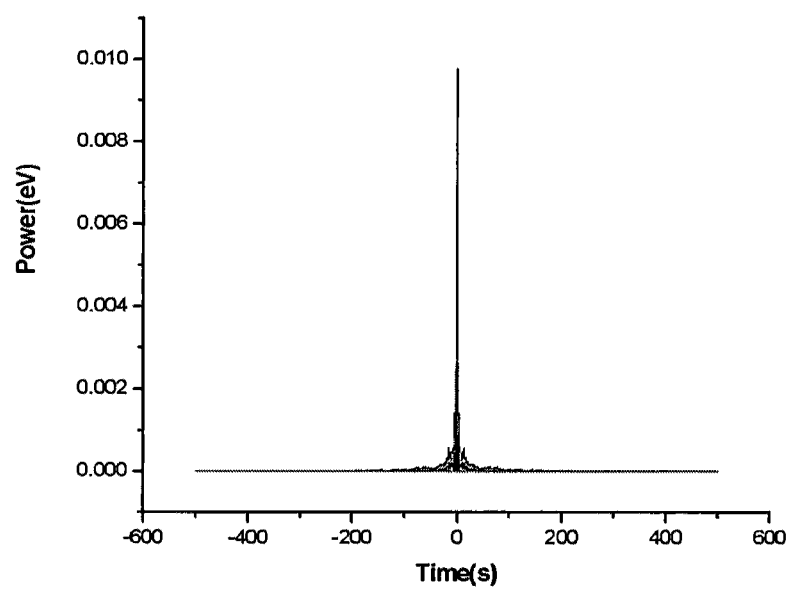

Preparing pharmaceutical solutions according to the pharmaceutical standards issued by the ministry of health in china as follows:
1. Preparing hydrochloride verapamil solution in the packet of 2.5 mg/5 ml.
2. Preparing hydrochloride isoprenaline solution in the packet of 2 mg/100 ml
3. Preparing physiological buffer superoxide dismutase solution in the packet of 1 mg/2 ml
4. Preparing physiological buffer adenosine triphosphate solution in the packet of 20 mg/3.3 ml
5. Respectively preparing the $10^{-23}$ M physiological buffer solutions of the 1-4 solutions
6. Respectively taking each pharmaceutical molecular numbers from the $10^{-23}$ M physiological buffer solutions according to the ratio of 1:0:0:1, mixing them at room temperature, adding physiological buffer solution up to 300 μl and keeping at −4° C. for applications
7. Employing semiconductor industry standards of cleaning silicon chip's surfaces and activating surfaces with hydrofluorine acids, preparing the P— and N-doped Si(100)-SiO$_2$ chips with massive hydrogen bonding as the substrates of self-directed and self-assembled quantum dots and monolayers. Under the class 10 clean environments, immersing the activated Si-chips into the optimum unitary, binary, ternary and quaternary pharmaceutical solutions for 12 hours according to the $L_{16}(2)^{15}$ and the $L_9(3)^4$, cleaning the surface three times with de-ionized sterile water, and drying the surface with nitrogen gas for characterizing by the C-AFM. The FIG. 6 shows the C-AFM topographic structure image; the FIG. 7d profiles the I-V curves of the quantized semiconductor conductance junction; the FIG. 8d is the differential conductance spectrum derived from the FIG. 7d, where covers the value of −0.84V threshold potential, the maximum conductance value of 49.07188 pA/V and the absolute value of Zeeman free energy |−3.35375|eV that is relevant to electron spin momentum, inelastic electron tunneling and charge transferring reactions; the FIG. 9g-h reveals frequency/time-energy spectra, where the central frequency/time value zero Hz/zero s that can be acquired from the central value of the area calculation in the frequency/time-energy spectra after the faster Fourier transformation of FIG. 8d, the highest occupied molecular orbit (HOMO)/conductance band(CB) value 0.03905 eV and the lowest unoccupied molecular orbit(LUMO)/valence band (VB) value 0.00976 eV that can be respectively acquired from the height values of the area calculation in the frequency-energy spectrum and time-energy spectrum after the faster Fourier transformation of FIG. 8d, and the absolute value of oxidative potential difference (0.13851−0.03463=0.10498 eV) that can be read out from the area difference between the frequency-energy spectrum and time-energy spectrum after the faster Fourier transformation of FIG. 8d.

The details of one or more embodiments of the invention are set forth in the accompanying drawings and the description. Other features, objects, and advantages of the invention will be apparent from the description and drawings, and from the claims.

The invention claimed is:
1. A quantized conductance junction, comprising:
   a monolayer formed by self-directing and self-assembling of biochemical compounds,
       wherein the biochemical compounds include one or more of superoxide dismutase, isoprenaline, adenosine triphosphate, and verapamil,
   the monolayer disposed on a substrate,
       wherein the biochemical compounds are hydrogen-bonded to the substrate, and unpaired electrons and π electrons of the biochemical compounds transition between the biochemical compounds and the substrate, and
   the substrate includes P— and N-doped Si—SiO$_2$.
2. A quantum logical switch, comprising the quantized conductance junction according to claim 1.
3. An array of quantized conductance junctions, comprising:
   the conductance junctions formed by a monolayer of self-directed and self-assembled biochemical compounds disposed on a substrate,
       wherein the biochemical compounds include one or more of superoxide dismutase, isoprenaline, adenosine triphosphate, and verapamil,
       wherein the biochemical compounds are hydrogen-bonded to the substrate, and unpaired electrons and π electrons of the biochemical compounds transition between the biochemical compounds and the substrate, and
   the substrate includes P—and N-doped Si—SiO$_2$.
4. The array of quantized conductance junctions according to claim 3, wherein the array has a height that includes one or more of 440 Å, 260 Å, 42 Å, and 17 Å.
5. The array of quantized conductance junctions according to claim 3, wherein the array has a height that includes one or more of 70 Å and 60 Å.
6. The array of quantized conductance junctions according to claim 3, wherein the monolayer has a thickness that includes one or more of 190 Å, 100 Å, 42 Å, 34 Å, and 18 Å.
7. The array of quantized conductance junctions according to claim 3, wherein each of the conductance junctions has a thickness that is 70 Å or 85 Å.
8. The array of quantized conductance junctions according to claim 3, wherein a thickness of the monolayer is 16 Å, wherein the conductance junctions include one or more of a Josephson junction, a negative differential conductance/resistance junction, and/or a zero-point motion junction.
9. The array of quantized conductance junctions according to claim 8, wherein a thickness of the negative differential conductance/resistance junction includes one or more of 400 Å, 55 Å, 42 Å, 36 Å, 23 Å, 21 Å, and 14 Å.

10. The array of quantized conductance junctions according to claim 8, wherein a thickness of the zero-point motion junction includes one or more of 32 Å, 28 Å, 26 Å, 22 Å, 20 Å, 19 Å, 15 Å, and 11.5 Å.

11. The array of quantized conductance junctions according to claim 8, wherein a thickness of the zero-point motion junction includes one or more of 70 Å, 55 Å, and 30 Å.

* * * * *

UNITED STATES PATENT AND TRADEMARK OFFICE
CERTIFICATE OF CORRECTION

PATENT NO.        : 8,431,338 B2                                                    Page 1 of 1
APPLICATION NO.   : 11/886490
DATED             : April 30, 2013
INVENTOR(S)       : Fang It is certified that error appears in the above-identified patent and that said Letters Patent is hereby corrected as shown below:

Title page, Item 73, after "Assignee:" delete "Zhonshan" and insert --Zhongshan--.

Signed and Sealed this
Twentieth Day of August, 2013

Teresa Stanek Rea
*Acting Director of the United States Patent and Trademark Office*